US010213583B2

(12) United States Patent
Klocke et al.

(10) Patent No.: US 10,213,583 B2
(45) Date of Patent: Feb. 26, 2019

(54) BALLOON CATHETER WITH TRANSIENT RADIOPAQUE MARKING

(71) Applicant: CLEARSTREAM TECHNOLOGIES LIMITED, Enniscorthy, County Wexford (IE)

(72) Inventors: Stephanie Klocke, Chandler, AZ (US); Rob Righi, Chandler, AZ (US)

(73) Assignee: CLEARSTREAM TECHNOLOGIES LIMITED, County Wexford (IE)

( * ) Notice: Subject to any disclaimer, the term of this patent is extended or adjusted under 35 U.S.C. 154(b) by 247 days.

(21) Appl. No.: 14/758,601

(22) PCT Filed: Dec. 31, 2013

(86) PCT No.: PCT/IB2013/003065
§ 371 (c)(1),
(2) Date: Jun. 30, 2015

(87) PCT Pub. No.: WO2014/102609
PCT Pub. Date: Jul. 3, 2014

(65) Prior Publication Data
US 2015/0335859 A1 Nov. 26, 2015

Related U.S. Application Data

(60) Provisional application No. 61/747,403, filed on Dec. 31, 2012.

(51) Int. Cl.
*A61M 25/01* (2006.01)
*A61M 25/10* (2013.01)
*A61F 2/82* (2013.01)

(52) U.S. Cl.
CPC .......... *A61M 25/0108* (2013.01); *A61F 2/82* (2013.01); *A61M 25/10* (2013.01); *A61M 25/104* (2013.01); *A61M 25/1011* (2013.01); *A61F 2210/0004* (2013.01); *A61F 2250/0098* (2013.01); *A61M 2025/105* (2013.01); *A61M 2025/1075* (2013.01); *A61M 2025/1079* (2013.01); *A61M 2025/1088* (2013.01)

(58) Field of Classification Search
CPC ...... A61F 2210/0004; A61F 2250/0098; A61F 2002/072; A61F 2/958; A61F 2/01; A61F 2002/016; A61F 2002/011; A61F 2/013; A61F 2/82; A61M 25/0108; A61M 25/104; A61M 2025/105; A61M 2025/1075;
(Continued)

(56) References Cited

U.S. PATENT DOCUMENTS 5,102,402 A 4/1992 Dror
5,257,974 A 11/1993 Cox
(Continued)

FOREIGN PATENT DOCUMENTS

JP 2011224357 A 11/2011

*Primary Examiner* — Katherine M Shi
(74) *Attorney, Agent, or Firm* — King & Schickli, PLLC

(57) ABSTRACT

Treating a treatment area in the vasculature includes a first catheter adapted for positioning at the treatment area, said first catheter including a first balloon having a transient radiopaque material corresponding to the treatment area. A second catheter adapted for positioning at the treatment area includes a treatment that substantially matches the transient radiopaque material, preferably so that the length and/or position of the treatment corresponds to the length and/or position of the transient radiopaque material. Related kits, assemblies, and methods are also described.

23 Claims, 10 Drawing Sheets

(58) Field of Classification Search
CPC .............. A61M 25/10; A61M 25/1011; A61M 2025/0008; A61M 2025/1031; A61M 2025/1086; A61M 29/02; A61B 2090/3966; A61B 90/39; A61B 17/12113; A61B 17/12031; A61B 17/12172; A61B 17/12109; A61B 2017/1205; A61B 17/12118
USPC ........... 604/96.01, 103.1; 606/191, 194, 198, 606/200; 623/1.11, 1.34, 1.38
See application file for complete search history.

(56) References Cited

U.S. PATENT DOCUMENTS

| | | |
|---|---|---|
| 5,405,378 A | 4/1995 | Strecker |
| 5,423,885 A | 6/1995 | Williams |
| 5,893,840 A | 4/1999 | Hull et al. |
| 6,626,939 B1 | 9/2003 | Burnside et al. |
| 7,879,011 B2 | 2/2011 | Chang |
| 7,951,194 B2 | 5/2011 | Gueriguian et al. |
| 8,162,880 B2 | 4/2012 | Jayaraman |
| 8,187,221 B2 | 5/2012 | Bates |
| 2006/0036316 A1* | 2/2006 | Zeltinger ............... A61L 31/18 623/1.49 |
| 2007/0112422 A1* | 5/2007 | Dehdashtian ............. A61F 2/24 623/2.11 |
| 2007/0288084 A1 | 12/2007 | Lee et al. |
| 2009/0149940 A1 | 6/2009 | Wang |
| 2009/0182404 A1 | 7/2009 | Shokoohi |
| 2009/0204203 A1 | 8/2009 | Allen |
| 2011/0009818 A1* | 1/2011 | Goff .................. A61M 25/0108 604/96.01 |
| 2012/0253451 A1 | 10/2012 | Sahatjian et al. |
| 2012/0259405 A1* | 10/2012 | Weber .................... A61F 2/848 623/1.15 |
| 2012/0265067 A1 | 10/2012 | Jayaraman |

* cited by examiner

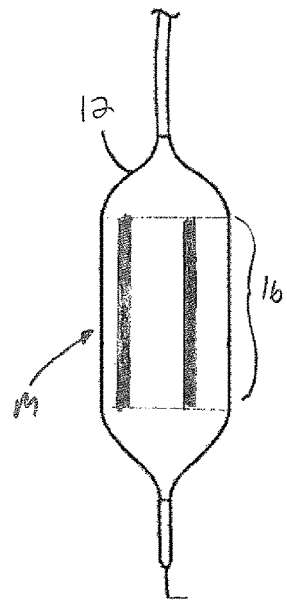
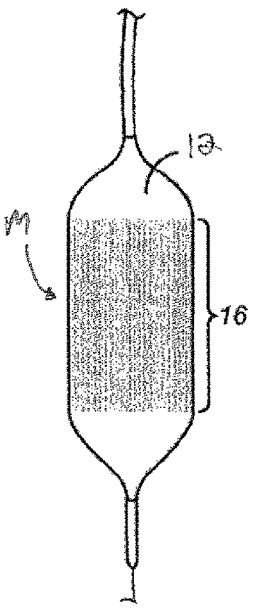
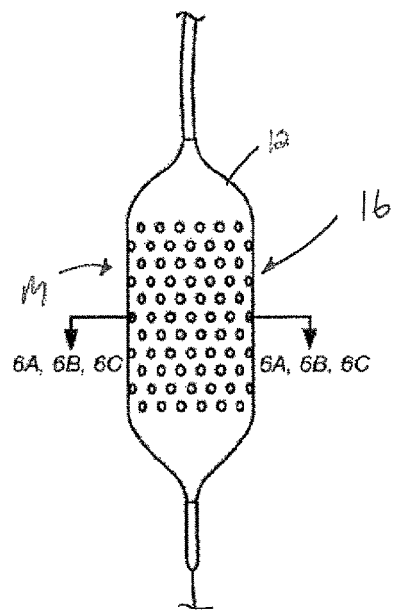
FIG. 5A          FIG. 5B          FIG. 5C
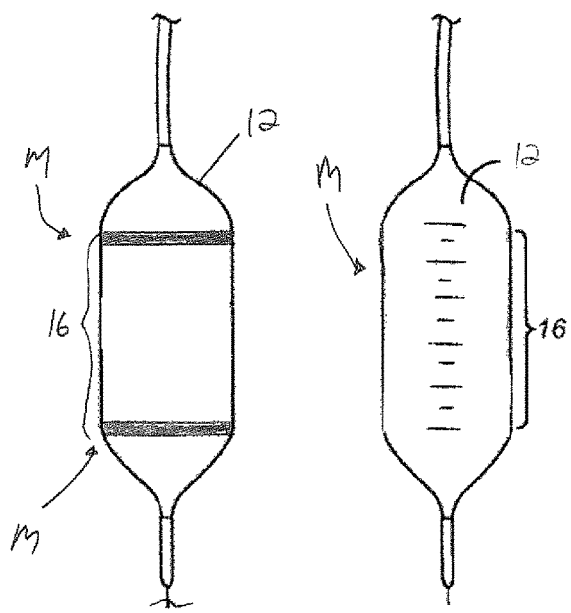
FIG. 5D          FIG. 5E ized by attaching marker bands on the catheter shaft corresponding to the ends of the balloon working surface. This "working surface" is the surface along the portion of the balloon that is used to achieve the desired treatment effect, such as contacting the calcified plaque (which surface in the case of a balloon having conical or tapering sections at the proximal and distal ends is typically co-extensive with a generally cylindrical barrel section).
BALLOON CATHETER WITH TRANSIENT RADIOPAQUE MARKING This application claims the benefit of U.S. Provisional Patent Application Ser. No. 61/747,403, which is incorporated herein by reference.

TECHNICAL FIELD

This disclosure relates generally to interventional medical procedures, such as angioplasty, and, more particularly, to a balloon catheter with a transient radiopaque marking.

BACKGROUND OF THE INVENTION

Catheters including balloons are routinely used to resolve or address flow restrictions or perhaps even complete blockages in tubular areas of a body, such as arteries or veins. In many clinical situations, the restrictions are caused by hard solids, such as calcified plaque, and may sometimes involve the use of high pressures to compact such blockages. Commercially available balloons employ complex technology to achieve high pressure requirements without sacrificing the profile of the balloon. Besides high pressure requirements, the balloons should also be resistant to puncture, easy to track and push, and present a low profile, especially when used for angioplasty.

The clinician performing the angioplasty procedure should be able to locate the position of the uninflated balloon with accuracy, so that the balloon will be properly positioned once inflated. This is conventionally accomplished by attaching marker bands on the catheter shaft corresponding to the ends of the balloon working surface. This "working surface" is the surface along the portion of the balloon that is used to achieve the desired treatment effect, such as contacting the calcified plaque (which surface in the case of a balloon having conical or tapering sections at the proximal and distal ends is typically co-extensive with a generally cylindrical barrel section).

However, misalignment of the marker bands during placement along the shaft sometimes results in their failure to correspond precisely to the extent of the working surface. This misalignment may prevent the clinician from accurately identifying the location of the working surface of the balloon during an interventional procedure. Also, when successive intravascular interventions are made, such as during a pre-dilatation using a first catheter followed by dilatation using a second catheter, the clinician must guess at the location where the pre-dilatation occurred. In any case, this uncertainty may lead to a geographic misalignment, or "miss," of the intended contact between the intended treatment area and the working surface of the balloon. It is especially desirable to avoid such an outcome when the balloon is designed to deliver a payload (such as a therapeutic agent (e.g., a drug, such as paclitaxel, rapamycin, heparin and the like), a stent, a stent graft, or a combination) or a working element (such as a cutter, focused force wire, or the like) to a specified location within the vasculature, since a miss may, at a minimum, prolong the procedure (such as, for example, by requiring redeployment of the balloon or the use of another balloon catheter in the case of a drug coated balloon), and possibly result in an inferior outcome if the lesion is not properly treated as a result of the misalignment.

In order to assess the length of a lesion from a location external to the body, a clinician may use an external ruler, which in one form is called a "LeMaitre" tape. While the use of such a ruler or tape may allow for a more precise assessment of the lesion length and an area treated by a pre-diliation step, it is not without limitations. For one, a displacement or difference in the apparent position of the lesion margins results when viewed along two different lines of sight. This "parallax" can lead to an inaccurate measurement and, at a minimum, contribute to the geographic misalignment of the working surface relative to the lesion. The use of such a ruler may also lead to inferior measurements when the vasculature at issue is particularly tortuous.

Accordingly, a need exists for a manner in which to position a balloon catheter into the vasculature at a treatment area with enhanced accuracy.

SUMMARY OF THE INVENTION

An object of the disclosure is to provide a catheter balloon with a transient radiopaque marking for use in marking a treatment area in the vasculature, which marking may then be used to ensure the accurate application of a treatment to the treatment area.

In one aspect, a kit for treating a treatment area in the vasculature is provided. The kit comprises a first catheter adapted for positioning at the treatment area, said first catheter including a first balloon having a transient radiopaque material corresponding to the treatment area, and a second catheter adapted for positioning at the treatment area. The second catheter may include a treatment that substantially matches the transient radiopaque material, preferably so that the length and/or position of the treatment corresponds to the length and/or position of the transient radiopaque material.

The second catheter may include one or more radiopaque markings for identifying the location of the treatment. A length of the transient radiopaque material may be substantially identical to a length of the treatment. The second catheter may include a second balloon having a working surface including the treatment. A position of the transient radiopaque material may correspond to an end of the working surface of the second balloon.

In any embodiment, the treatment may be selected from the group consisting of a drug, a stent, a stent graft, a cutter, a focused force wire, or any combination thereof. In any case, a length of the treatment may substantially match the length of the transient radiopaque marking. The transient radiopaque marking may be a material selected from the group consisting of a radiopaque dye, powder, or gel. A bioresorbable stent may include the transient radiopaque marking, or the transient radiopaque marking may comprise a layer of the first balloon.

Another aspect of the disclosure pertains to a kit for treating a treatment area in the vasculature. The kit comprises a first catheter adapted for positioning at the treatment area in the vasculature. The first catheter includes a first balloon having a transient radiopaque material having first and second ends corresponding to the treatment area. A second catheter adapted for positioning at the treatment area includes a treatment having first and second ends corresponding to the first and second ends of the transient radiopaque material.

The second catheter may include one or more radiopaque markings for identifying the location of the treatment. A length of the transient radiopaque material may be substantially identical to a length of a first working surface of the first balloon. The treatment may be selected from the group consisting of a drug, a stent, a stent graft, a cutter, a focused force wire, or any combination thereof. A length of the treatment may substantially match the length of the transient radiopaque marking. The transient radiopaque marking may comprise a strip, band, or pattern of a radiopaque material.

The second catheter may include a second balloon having a working surface including the treatment. The transient radiopaque marking may be coated over at least a portion of the first balloon, disposed in a porous structure of the first balloon, disposed in wells on the first balloon, provided as a plurality of microdots on the first balloon, present on the first balloon under a membrane, or any combination thereof. The transient radiopaque marking may be permanent.

A further aspect of the disclosure relates to a method of performing an intervascular procedure at a treatment area. The method comprises the steps of transferring a transient radiopaque material corresponding to the treatment area from a first balloon to the treatment area, and providing a treatment to the treatment area, the treatment corresponding in length to the transient radiopaque material.

The treatment area may be a lesion having a length, and including the step of providing the treatment corresponding to the length of the lesion. The method may also comprise providing the transient radiopaque marking corresponding to the length of the lesion. The method may further include the step of providing the transient radiopaque marking bounding a working surface of the first balloon. The step of providing the treatment may include providing a therapeutic agent, a stent, a stent graft, a cutter, a focused force wire, or any combination thereof. The step of providing the treatment may also comprise providing a second balloon on the catheter.

A further aspect of the disclosure relates to a kit for treating a treatment area in the vasculature. The kit comprises a first catheter adapted for positioning at the treatment area, said first catheter including a first balloon having a transient radiopaque material corresponding to the treatment area, and a second catheter adapted for positioning at the treatment area, said second catheter including a therapeutic agent that substantially corresponds to the transient radiopaque material, preferably so that the length and/or position of the therapeutic agent corresponds to the length and/or position of the transient radiopaque material. The therapeutic agent may be selected from the group consisting of paclitaxel, rapamycin, heparin, or any combination thereof, and the second catheter may include a balloon carrying the therapeutic agent.

Still a further aspect of the disclosure relates to a kit for treating a treatment area in the vasculature. The kit comprises a first catheter adapted for positioning at the treatment area in the vasculature, said first catheter including a first balloon having a first, transient radiopaque material corresponding to the treatment area, and a second catheter adapted for positioning at the treatment area. The second catheter includes a second balloon having a working surface identified by a second radiopaque marking. The second radiopaque marking may include at least two bands formed of a radiopaque material connected to a tube of the second catheter.

A further aspect of the disclosure pertains to an assembly for treating a treatment area in the vasculature, comprising: a first catheter adapted for positioning at the treatment area in the vasculature, said first catheter including a first balloon having a transient radiopaque material corresponding to the treatment area; and a second catheter adapted for positioning at the treatment area, said second catheter including a treatment that substantially corresponds to the transient radiopaque material, preferably so that the length and/or position of the treatment corresponds to the length and/or position of the transient radiopaque material. The second catheter may include a second balloon having a working surface when inflated, the working surface including the treatment.

BRIEF DESCRIPTION OF THE FIGURES

FIGS. 5A to 5G show details of a first catheter used in embodiments of the present disclosure.

MODES FOR CARRYING OUT THE INVENTION

The description provided below and in regard to the figures applies to all embodiments unless noted otherwise, and features common to each embodiment are similarly shown and numbered.

Figure 1:
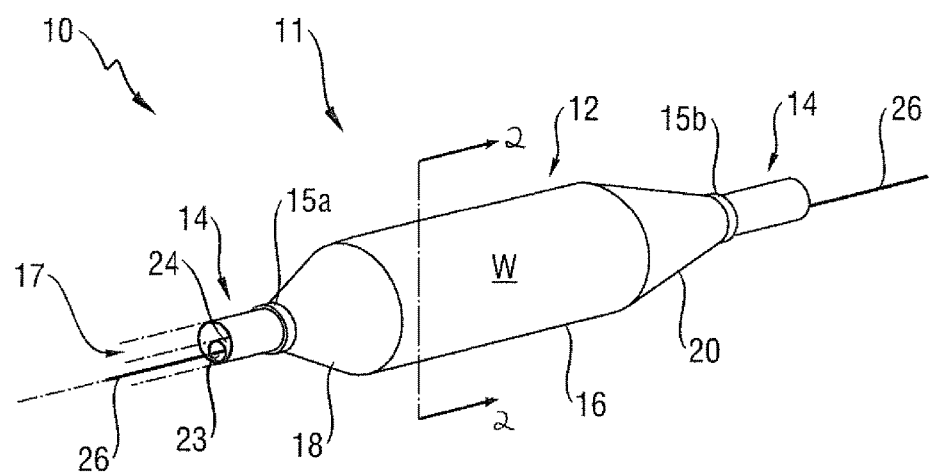
FIGS. 1 to 4 show a catheter used in embodiments of the present disclosure.
Figure 2:
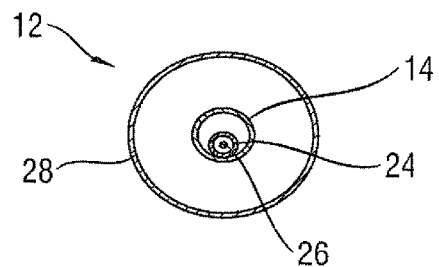
Figure 3:
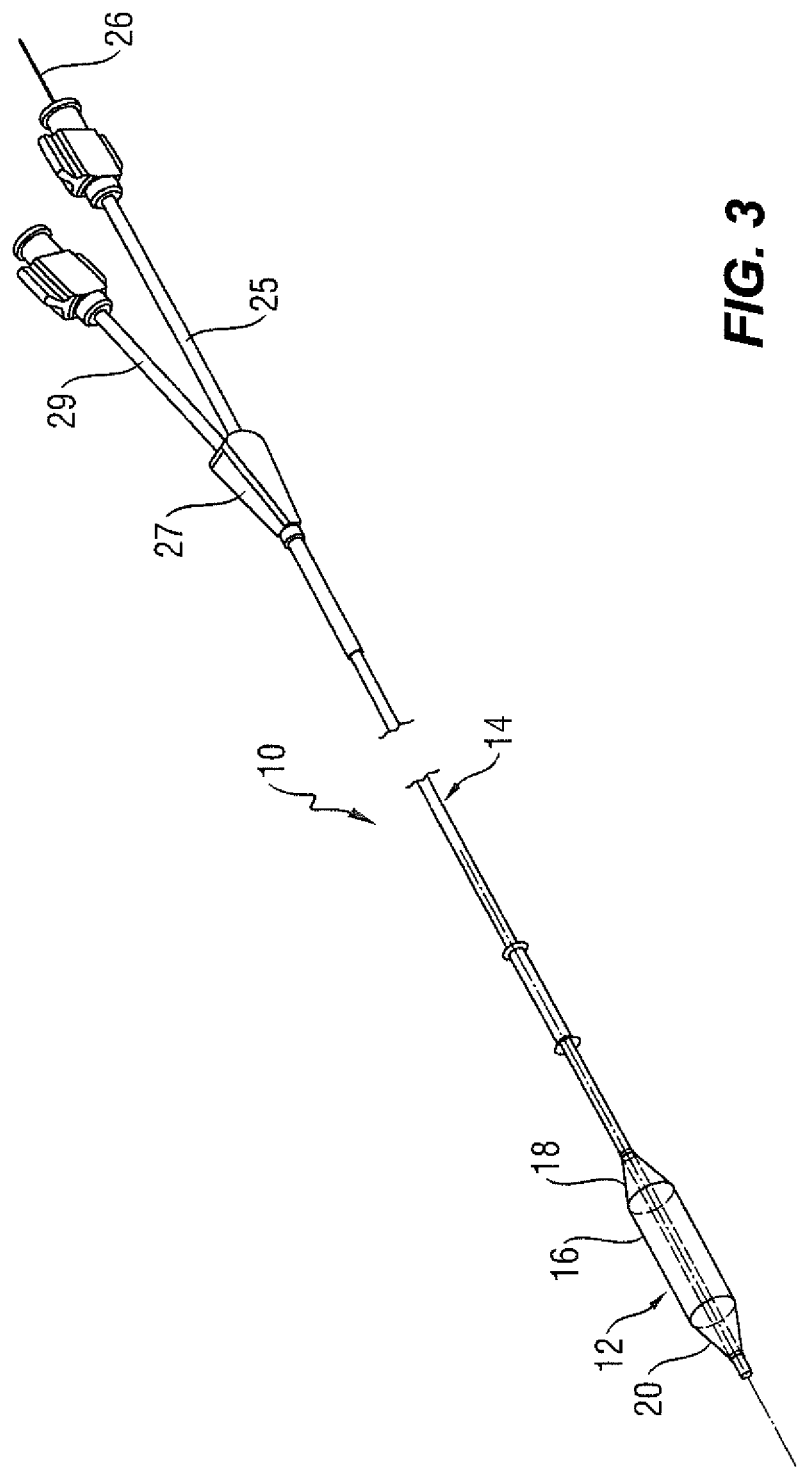

Provided is a catheter 10 having a distal portion 11 with a balloon 12 mounted on a catheter tube 14. Referring to FIGS. 1, 2, and 3, the balloon 12 has an intermediate section 16, or "barrel" having a working surface W, and end sections 18, 20. In one embodiment, the end sections 18, 20, taper or reduce in diameter to join the intermediate section 16 to the catheter tube 14 (and thus sections 18, 20 are generally termed cones or cone sections). The balloon 12 is sealed to catheter tube 14 at balloon ends (proximal 15a and distal 15b) on the end sections 18, 20 to allow the inflation of the balloon 12 via one or more inflation lumens 17 extending within catheter tube 14 and communicating with the interior of the balloon 12.

Figure 4:
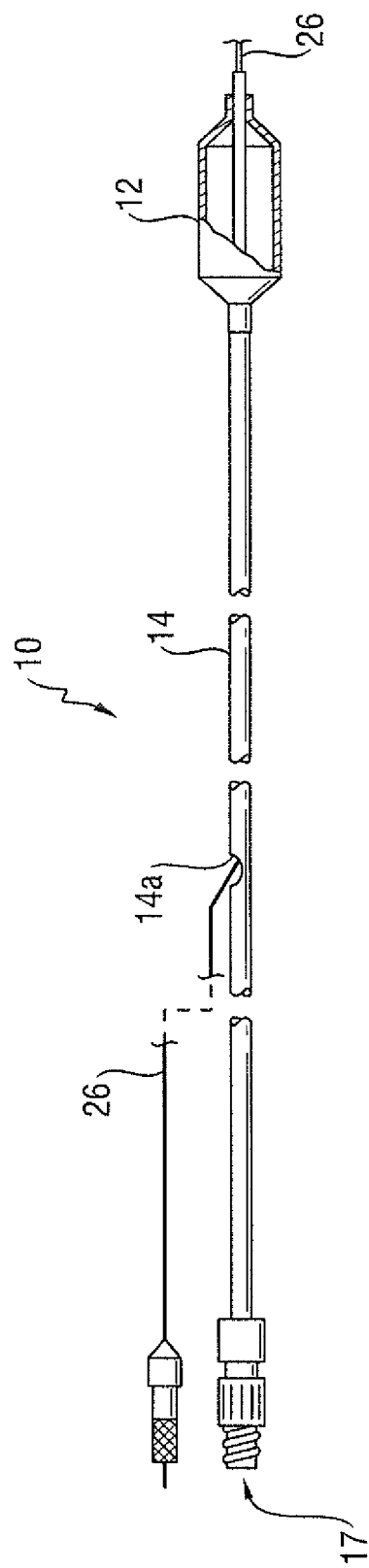

The catheter tube 14 also includes an elongated, tubular shaft 24 forming a guidewire lumen 23 that directs the guidewire 26 through the catheter 10. As illustrated in FIG. 3, this guidewire 26 may be inserted through a first port 25 of a connector 27 into the lumen 23 to achieve an "over the wire" (OTW) arrangement, but could also be provided in a "rapid exchange" configuration in which the guidewire 26 enters the lumen 23 through a lateral opening 14a closer to the distal end (see FIG. 4). A second port 29 may also be associated with catheter 10, such as by way of connector 27, for introducing a fluid (e.g., saline, a contrast agent, or both) into the interior of the balloon 12 via the inflation lumen 17.

Balloon 12 may include a single or multi-layered balloon wall 28. The balloon 12 may be a non-compliant balloon having a balloon wall 28 that maintains its size and shape in one or more directions when the balloon is inflated. The balloon 12 in such case also has a pre-determined surface area that remains constant during and after inflation, also has a pre-determined length and pre-determined circumference that each, or together, remain constant during and after inflation. However, the balloon 12 could be semi-compliant or compliant instead, depending on the particular use.

The balloon 12 may be provided with a radiopaque material adapted for contacting a treatment area in order to at least partially transfer the material thereto and form a radiopaque marking M that can be perceived under fluoroscopy (see FIGS. 10-12 and the corresponding discussion below). This temporary marking M may be achieved by providing a transient radiopaque material on the outer surface of the balloon 12 and, in particular, along the barrel section 16 between its ends. The skilled person will understand from that sentence that a "transient" material is a material producing a marking which may or may not be permanent.

Figure 5F:
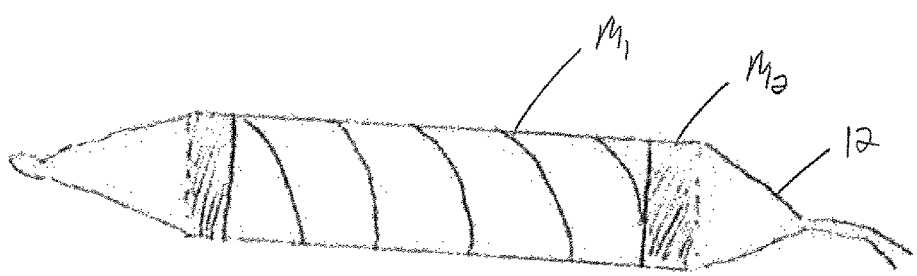
Figure 5G:

As shown in FIGS. 5A-5G, this marking M may be provided in various shapes or sizes, including for example as one or more longitudinal strips (FIG. 5A), full coverage of the barrel section 16 corresponding to the working surface W (FIG. 5B), a pattern (FIG. 5C), one or more circumferential bands (FIG. 5D), or hash lines that may provide a ruler function (FIG. 5E), or any combination of the foregoing. Combinations of markings M1, M2, can be used as shown in FIG. 5F, in order to more clearly differentiate among different locations or parts of the working surface W of the balloon 12 (e.g., the terminal ends of the barrel section 16, which as will be understood upon reviewing the description that follows may correspond identically to a balloon subsequently used for treating the treatment area). Also, as shown in FIG. 5G, the marking M may comprise a bioresorbable stent 39 that is transferred to the treatment area in order to provide the desired radiopaque quality prior to the treatment (see, e.g., U.S. Pat. No. 7,951,194, the disclosure of which is incorporated herein by reference).

The radiopaque material may be sequestered or otherwise immobilized on the external surface of the balloon 12 in a variety of ways. For example, the radiopaque material may be a conventional radiopaque dye, which may be coated over a portion of the surface of the balloon 12, either with or without a suitable carrier compound. The radiopaque materials may also be used in the form of gels, powders, dust, particles, nano-particles, liquids, stains, adhesives and the like. The material could be anywhere from about 5-95% radiopaque or, more specifically, in the range of about 70-90% radiopacity. The radiopaque material could be one of many currently in use in medicine, including but in no way limited to: iodine, iopromide, metallic ions, gold, barium sulfate, or other similarly functional materials. In one embodiment, a biocompatible adhesive could be mixed with the radiopaque material to promote adherence to the target area. The persistence of the dye or other radiopaque material could be temporary in nature, designed to last long enough to aid the procedure, or could be permanent.

At least a portion of the surface of the balloon 12 could be treated with folds or mini-folds designed to harbor the radiopaque material forming the transient marking M during delivery to the treatment area. Alternatively, the surface of the balloon 12 could be treated to have a surface geometry designed to hold the radiopaque material substantially in place until deployment at the target site. This surface treatment could include wells or micro-wells filled with the radiopaque material. The surface treatment could also include fine, hair-like structures coated with radiopaque material and designed to optimize surface contact and transfer. Further, these fine, hair-like structures could be made of radiopaque material and designed to separate from the balloon 12 and attach to the target tissue. The balloon surface could have raised micro-dots of radiopaque element in a gel form. These micro-dots of radiopaque gel could include adhesive properties to help attach to the contact surfaces within the body.

Alternatively, the balloon 12 could be constructed from several layers of material, with the inner layers providing the desired expansion properties. The outermost layer of the balloon 12 could be made of an absorbent material preloaded with radiopaque material so as to provide the transient marking M. This material could have sponge-like characteristics, which may contain pores filled with radiopaque dye. These pores could enclose the radiopaque gel of the uninflated balloon 12. Upon inflation, the pores may compress and force the radiopaque material onto the treatment area.

Figure 6B:
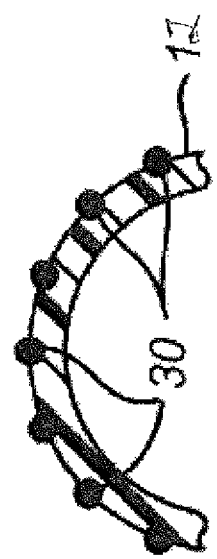
FIGS. 6A to 6C show details of surface treatments used in catheters used in embodiments of the present disclosure.
Figure 6C:
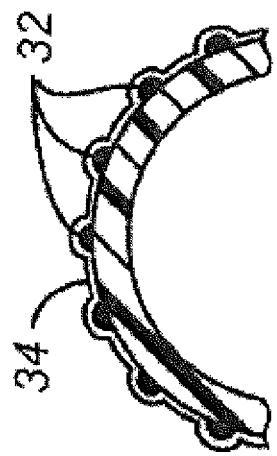
Figure 6A:
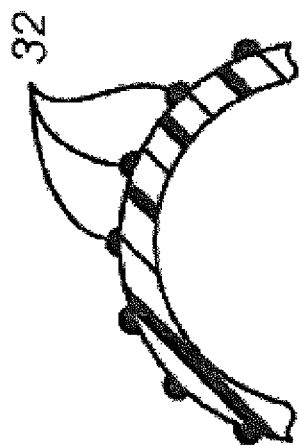
Figure 7A:
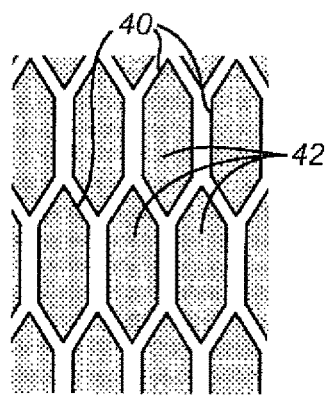
FIGS. 7A to 9B show details of further surface treatments used in catheters used in embodiments of the present disclosure.
Figure 7B:
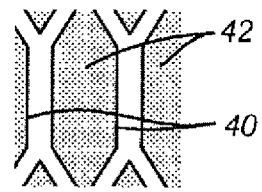

FIGS. 6A-6C show three specific examples of potential surface treatments applied to balloon 12 to enhance the delivery and transfer of the radiopaque material. As shown in FIG. 6A, indented wells 30 can be formed over the central section 16 of the balloon surface to contain the radiopaque material. As shown in FIG. 6B, raised dots 32 could consist of a gel mixed with the radiopaque material. Such dots or microdots can be formed into adherent admixtures applied as droplets and fixed to the surface of the balloon 12 upon drying or curing. As shown in FIG. 6C, the radiopaque material can be maintained on the external surface of the balloon using a membrane 34. The radiopaque material may comprise microdots 32 or other layers or sources of the radiopaque material FIGS. 7A and 7B illustrate that the external balloon surface, or another layer of material applied over the balloon surface, can be formed with sponge-like pores 40 which hold the radiopaque material 42. When the balloon is unexpanded, as shown in FIG. 7A, the radiopaque material 42 is held tightly within the pores. When the balloon is expanded, as shown in FIG. 7B, however, the pores stretch and expose the radiopaque material facilitating its release.

Figure 8A:
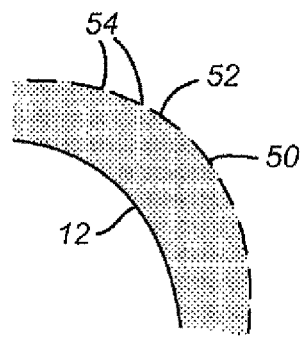
Figure 8B:
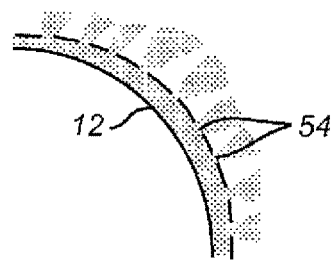
Figure 10:
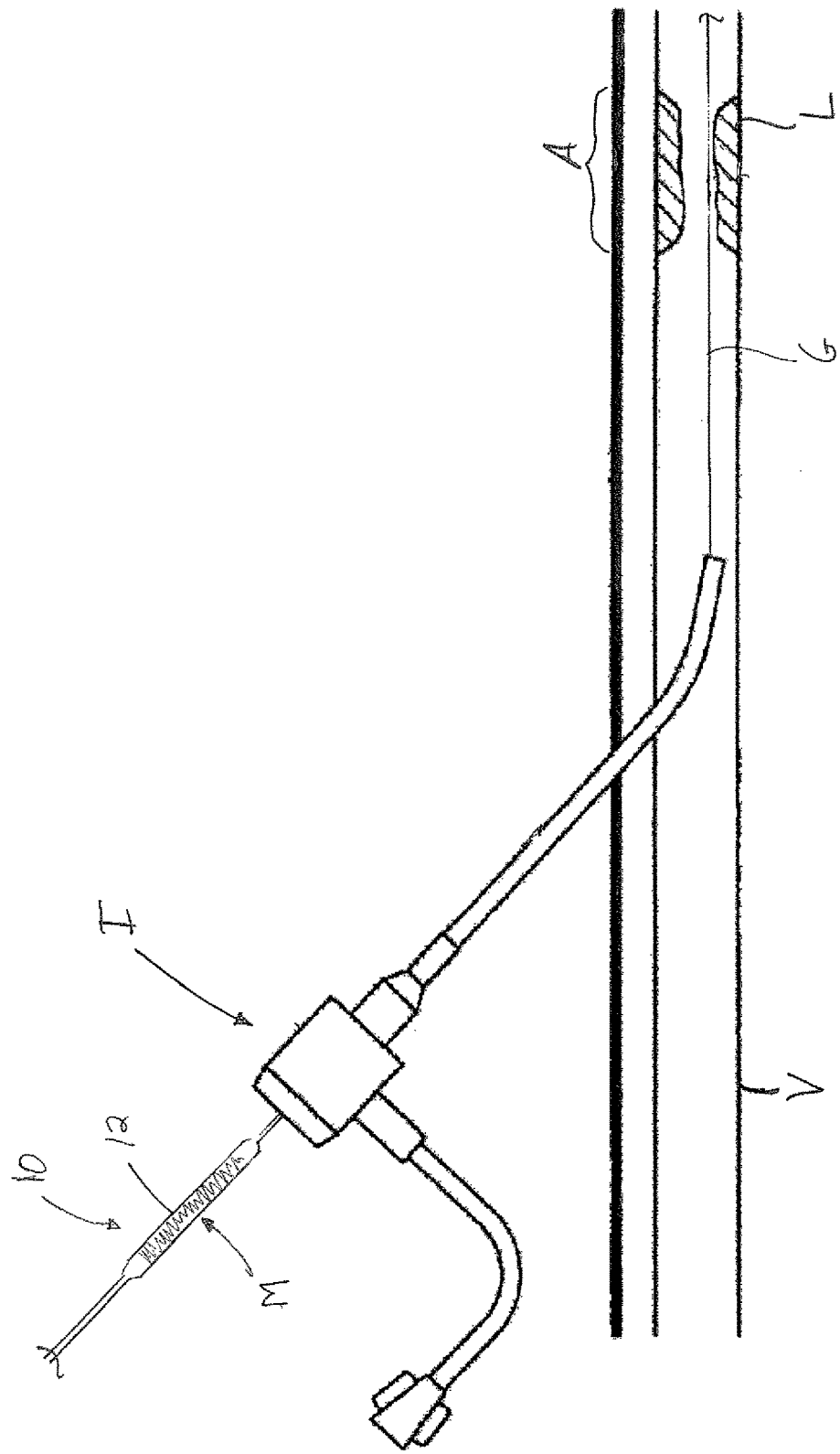
FIGS. 10 to 12 show a way in which a catheter kit according to embodiments of the present disclosure is used.

As shown in FIGS. 8A and 8B, the radiopaque material 50 may be layered over the balloon 12 with an outer, perforated layer 52 holding the radiopaque material in place, as shown in FIG. 10. Upon balloon expansion, as shown in FIG. 8A, the balloon 12 expands and forces the radiopaque material 50 out through the perforations 54 in the outer layer 52, releasing the radiopaque dye as shown in FIG. 8B.

Figure 9A:
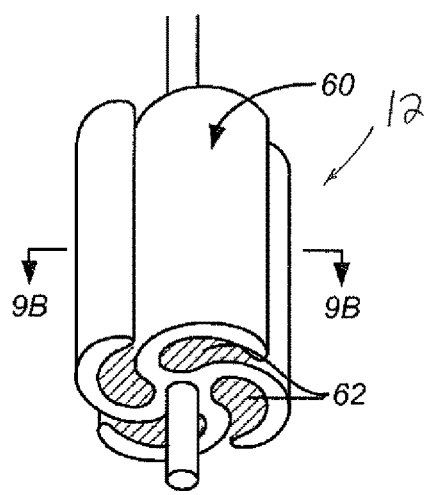
Figure 9B:
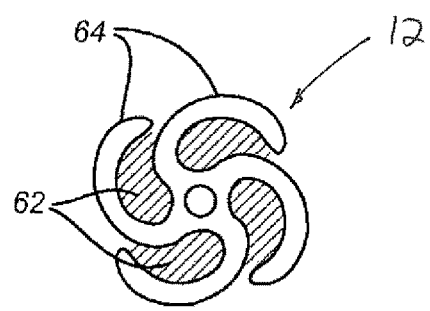

FIGS. 9A and 9B show a balloon 12 folded for delivery. The balloon 12 could be folded during manufacturing. The radiopaque material 62 is sequestered between folds or "lobes" 60 of the balloon 12. This configuration allows the radiopaque material 62 to be delivered to the treatment area site without being lost through contact with other surfaces. The material 62 is then released upon balloon inflation.

The radiopaque material forming the transient marking M could be suspended in an aqueous solution applied to the surface during manufacturing and allowed to dry, evaporating off the water and leaving the radiopaque dye in place. Likewise, a solution based on acetone or isopropyl alcohol may speed the evaporation process. Radiopaque paint, varnish, resin, lacquer, polymer could be applied to the balloon 12. The radiopaque material could also be applied using vapor deposition, static deposition, or during a controlled coasting, spraying, dipping, molding, or heating process. Alternatively, the radiopaque element could be combined with an ultraviolet sensitive substrate, applied to the device, and cured into place using UV curing processes.

In another approach, sheets of radiopaque material could be fabricated in a separate process, and the sheets then attached to the balloon 12 using adhesive, radio-frequency welding, thermal bonding or similar techniques. In still another approach, the radiopaque material could be combined with a substance which specifically or preferentially binds to tissue in the treatment area. Alternatively, radiopaque dye can be suspended in a biocompatible hydrogel and freeze-dried to form a solid that can be attached to the balloon 12. Upon sufficient combination with the fluids and heat of the body, the solid would liquefy, releasing the radiopaque material onto the target area. Additionally, the radiopaque element could be a powder, dust, or flakes applied to the surface of the balloon 12.

Figure 11:
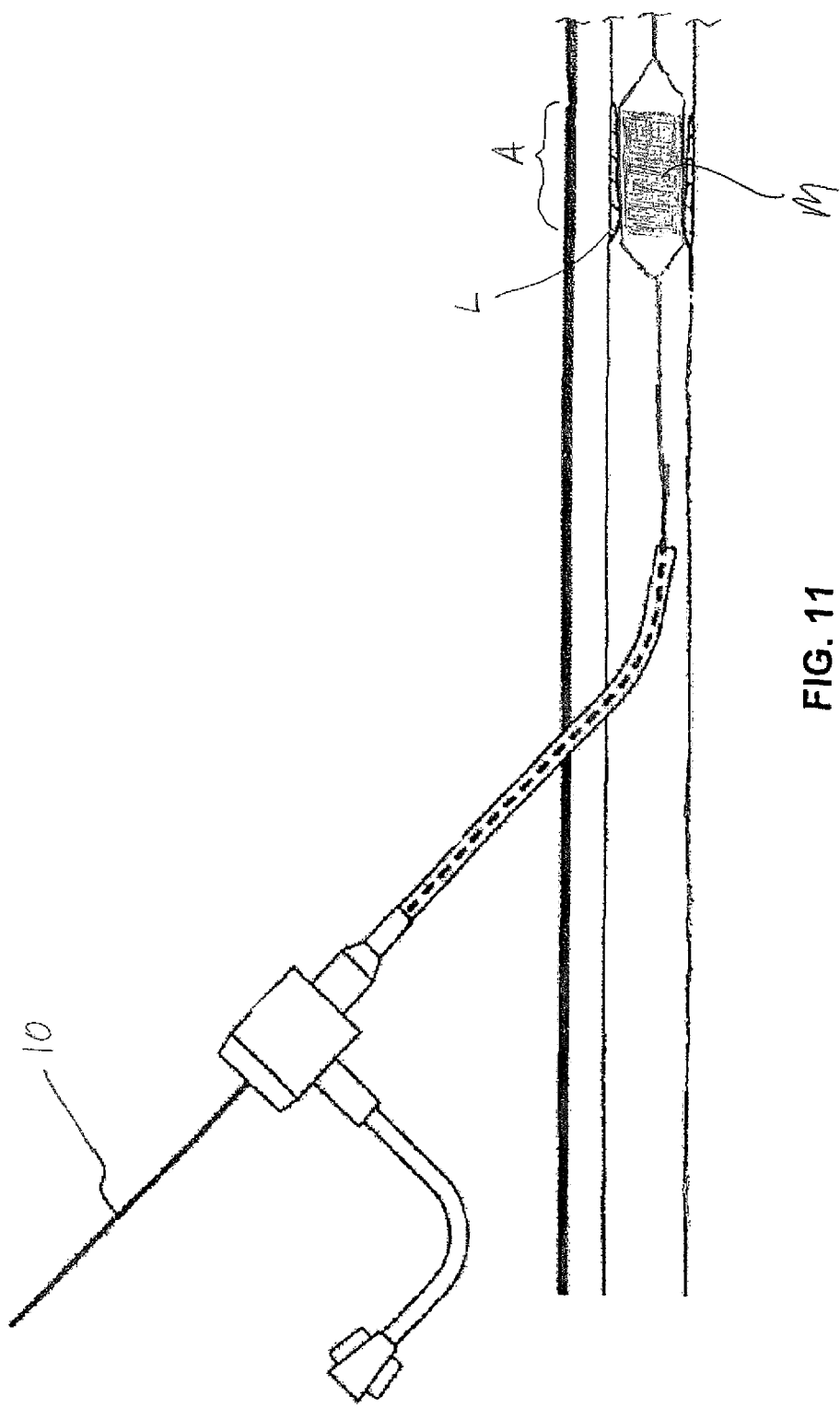
Figure 12:
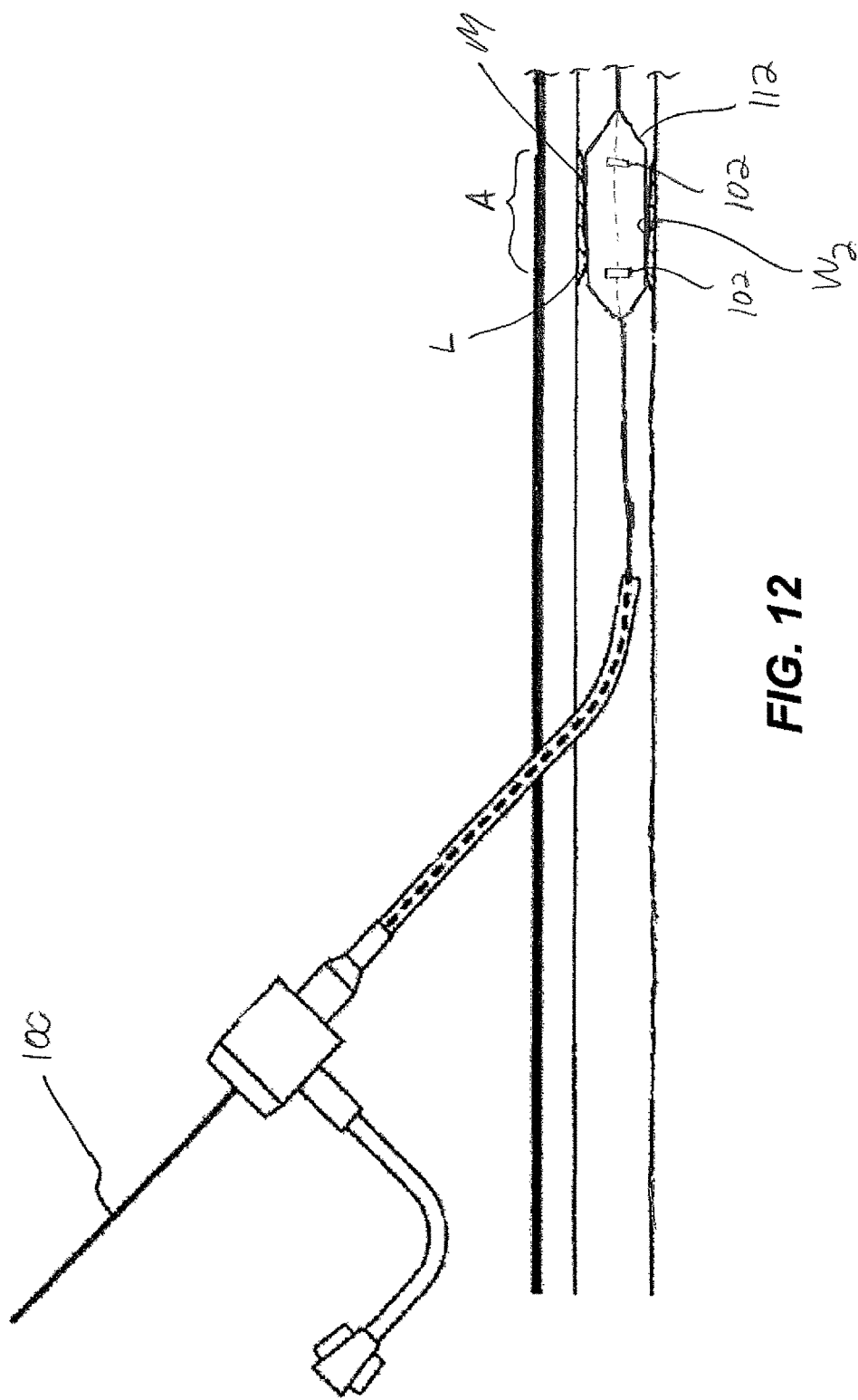

FIGS. 10-12 illustrate uses of a balloon 12 with a transient radiopaque marking M. FIG. 10 shows a folded balloon 12 of catheter 10 including marking M being inserted along a guidewire G into a vessel V to a treatment area A, such as a lesion L, using a device called an introducer I. The marking M is provided on the balloon 12 such that it corresponds to the treatment area A (such as by defining at least the ends, and thus also substantially matches the ends or length of the working surface on a second balloon, which as noted below may provide dilatation and be provided during the same or a subsequent intervention). Upon this first balloon 12 being at least partially inflated, as shown in FIG. 11, the transient radiopaque marking M is thus transferred to the treatment area A, but in a manner that is temporary rather than permanent. The balloon 12 may then be deflated, wrapped or folded, and withdrawn.

As shown in FIG. 12, a treatment catheter 100 (which may be substantially identical in construction to catheter 10) may then be inserted to position a treatment balloon 112 at the treatment area A. This second balloon 112 may include a working surface W2 including a treatment, such as for example a therapeutic agent (e.g., a drug, such as paclitaxel, rapamycin, heparin and the like), a stent, a stent graft, or a combination) that corresponds to the treatment area A, such as in size (e.g., length). Using fluoroscopy, the clinician may match markings on this catheter 100 (such as permanent bands 102 made of a radiopaque material and substantially matching the ends of the working surface W2 when the corresponding balloon 112 is inflated) with the now-transferred marking M in the vessel V corresponding to the treatment area A. When the balloon 112 is subsequently inflated to provide the treatment to the treatment area A (which may also involve fully compacting the lesion L), the clinician is assured that the delivery is achieved in the intended manner to the entire treatment area A, but not elsewhere, which may aid in avoiding geographic misalignment. Consequently, the procedure is potentially shortened, and a further intervention may be avoided.

While the disclosure presents certain embodiments to illustrate the inventive concepts, numerous modifications, alterations, and changes to the described embodiments are possible without departing from the sphere and scope of the present invention, as defined in the appended claims. For example, any ranges and numerical values provided in the various embodiments are subject to variation due to tolerances, due to variations in environmental factors and material quality, and due to modifications of the structure and shape of the balloon, and thus can be considered to be approximate and the term "approximately" means that the relevant value can, at minimum, vary because of such factors. Also, the drawings, while illustrating the inventive concepts, are not to scale, and should not be limited to any particular sizes or dimensions. Accordingly, it is intended that the present disclosure not be limited to the described embodiments, but that it has the full scope defined by the language of the following claims, and equivalents thereof.

The invention claimed is:

1. A kit for treating a treatment area in the vasculature, comprising:
a first catheter adapted for positioning at the treatment area, said first catheter including a first balloon having a transient radiopaque material corresponding to the treatment area;
and
a second catheter adapted for positioning at the treatment area, said second catheter having a treatment that substantially matches the transient radiopaque material while on the first balloon, so that the length or position of the treatment corresponds to the length or position of the treatment area.

2. The kit of claim 1, wherein the second catheter includes one or more radiopaque markings for identifying the location of the treatment.

3. The kit of claim 1, wherein a length of the transient radiopaque material is substantially identical to a length of the treatment.

4. The kit of claim 1, wherein the second catheter includes a second balloon having a working surface including the treatment.

5. The kit of claim 4, wherein a position of the transient radiopaque material corresponds to an end of the working surface of the second balloon.

6. The kit of claim 1, wherein the treatment is selected from the group consisting of a drug, a stent, a stent graft, a cutter, a focused force wire, or any combination thereof.

7. The kit of claim 6, wherein a length of the treatment substantially matches the length of the transient radiopaque material.

8. The kit of claim 1, wherein the transient radiopaque material is selected from the group consisting of a radiopaque dye, powder, or gel.

9. The kit of claim 1, further including a bioresorbable stent including the transient radiopaque material.

10. The kit of claim 1, wherein the transient radiopaque material comprises a layer of the first balloon.

11. The kit of claim 1, wherein the transient radiopaque material comprises a strip or band.

12. The kit of claim 1, wherein the transient radiopaque material is coated over at least a portion of the first balloon, disposed in a porous structure of the first balloon, disposed in wells on the first balloon, provided as a plurality of microdots on the first balloon, present on the first balloon under a membrane, or any combination thereof.

13. The kit of claim 1, wherein the transient radiopaque material is permanent.

14. The kit of claim 1, wherein the treatment comprises a therapeutic agent selected from the group consisting of paclitaxel, rapamycin, heparin, or any combination thereof.

15. The kit of claim 14, wherein the second catheter includes a balloon carrying the therapeutic agent.

16. The kit of claim 1, wherein the second catheter includes markings that match the location of the transient radiopaque material of the first catheter.

17. A kit for treating a treatment area in the vasculature, comprising:
a first catheter adapted for positioning at the treatment area in the vasculature, said first catheter including a first balloon having a transient radiopaque material having first and second ends corresponding in size to the treatment area;
and
a second catheter adapted for positioning at the treatment area, said second catheter including a treatment having first and second ends corresponding to the first and second ends of the transient radiopaque material on the first balloon.

18. The kit of claim 17, wherein the second catheter includes one or more radiopaque markings for identifying the location of the treatment.

19. The kit of claim 17, wherein the treatment is selected from the group consisting of a drug, a stent, a stent graft, a cutter, a focused force wire, or any combination thereof.

20. The kit of claim 19, wherein a length of the treatment substantially matches the length of the transient radiopaque material.

21. The kit of claim 17, wherein the second catheter includes a second balloon having a working surface including the treatment.

22. A kit for treating vasculature comprising a balloon catheter and a second catheter
   wherein
      the balloon catheter has a balloon with a surface having transient radiopaque material in a pattern,
      and
      the balloon catheter is adapted to mark vasculature in the pattern with transient radiopaque material,
   and
   wherein the second catheter comprises a treatment corresponding in length to the pattern while on the balloon.

23. A kit for treating vasculature at a treatment area, comprising:
   a first catheter adapted for positioning at the treatment area, the first catheter including a first balloon having a transient radiopaque material corresponding to the treatment area;
   and
   a second catheter adapted for positioning at the treatment area, the second catheter having a treatment wherein the treatment substantially matches the transient radiopaque material in length while on the first balloon.

* * * * *